United States Patent [19]

Bader et al.

[11] Patent Number: 5,177,255
[45] Date of Patent: Jan. 5, 1993

[54] BIS-STILBENE COMPOUNDS

[75] Inventors: Axel Bader, Leverkusen; Dieter Arlt, Cologne; Florin Seng, Bergisch-Gladbach, all of Fed. Rep. of Germany

[73] Assignee: Bayer Aktiengesellschaft, Leverkusen, Fed. Rep. of Germany

[21] Appl. No.: 704,748

[22] Filed: May 23, 1991

[30] Foreign Application Priority Data

May 31, 1990 [DE] Fed. Rep. of Germany ....... 4017568

[51] Int. Cl.$^5$ ............................................. C07C 143/38
[52] U.S. Cl. ........................................ 562/87; 562/85; 562/88; 252/301.21
[58] Field of Search ................ 562/88, 45, 87; 252/301.21

[56] References Cited

U.S. PATENT DOCUMENTS 4,339,238  7/1982  Fringeli et al. .

FOREIGN PATENT DOCUMENTS 0032483  7/1981  European Pat. Off. .
0364403  4/1990  European Pat. Off. .
1025465  6/1981  Japan ..................... 582/77
0640899  1/1984  Switzerland .

OTHER PUBLICATIONS

Chemical Abstract 102:76417m (1985). ·
Chemical Abstract 104:49208d (1986).

*Primary Examiner*—Asok Pal
*Attorney, Agent, or Firm*—Sprung Horn Kramer & Woods

[57] ABSTRACT

Sulphonic acids of bis-styrylbiphenyls, which are useful optical brighteners, are obtained in good yields in a simple manner by reacting styrene compounds with 4,4'-dibromobiphenyl-3,3'-disulphonic acids or their salts in the presence of bases and palladium catalysts.

The bis-stilbene compounds have the formula:

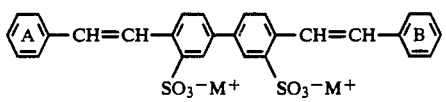

where at least one of the rings A or B contains a sulfonic acid group.

3 Claims, No Drawings

BIS-STILBENE COMPOUNDS

SUMMARY OF THE INVENTION

The invention relates to bis-stilbene compounds of the formula

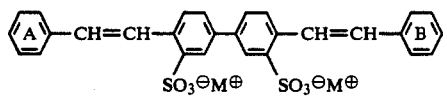

in which $M^\oplus$ denotes a cation and at least one of the rings A or B contains a sulpho group.

These compounds have a stronger brightening power than those conventionally used for synthetic fibres, in particular cellulose or polyamide fibres. The compounds according to the invention can be prepared by a large number of processes which are known per se.

An industrially utilisable and advantageous process comprises reacting a compound of the general formula

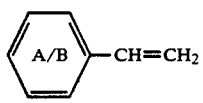

with halogen compounds of the formula (III)

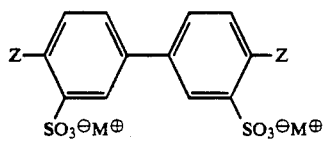

where

Z represents Cl, Br or I and the other symbols have the abovementioned meaning, in the presence of a base and a palladium complex or a combination of compounds forming this complex.

This reaction is known in principle for specific olefins (compare J. Amer. Chem. Soc. 96, 1133 (1974) and U.S. Pat. Specif. No. 3,922,299).

DETAILED DESCRIPTION OF THE INVENTION

Suitable organophosphine-palladium complexes are, for example, those of the formula $$X_2Pd(PR_3)_2$$

where

X denotes halogen, cyano, nitro or (OOC—$C_1$—$C_{1-2}$—alkyl) and

R denotes aryl, alkoxy, alkyl or phenoxy.

Suitable compounds which form this catalyst are combinations of palladium compounds and phosphines or phosphites.

Examples of such palladium compounds are:
$PdCl_2$, $PdBr_2$, $Pd(CN)_2$, $Pd(NO_3)_2$,

$Pd(OOC-C_{1-12}-alkyl)_2$, particularly palladium acetate. However, palladium(0) complexes, such as, for example, bis-(dibenzylideneacetone)palladium(0), bis-(phenylisonitrile)palladium(0) and tetrakis(triphenylphosphine)palladium are also suitable.

Examples of the phosphorus compounds which may be mentioned are:

diphenylmethyl-phosphine, diphenylmethoxyphosphine, trimethylphosphine, triethylphosphine, tri-n-butylphosphine, triphenylphosphine, phenyl-di-n-butoxyphosphine, tri-o-tolylphosphine and triphenyl phosphite. The trialkyl- and triphenylphosphines are preferred.

Cyclic and N,N-disubstituted amides are highly suitable as a reaction medium.

Examples which may be mentioned are:

N,N-dimethylformamide, N,N-diethylformamide, N,N-di-nbutylformamide, N,N-diisopentylformamide, N,N-dimethylacetamide, N,N-dimethylpropionamide, N-methyl-N-benzylformamide, N-ethyl-N-cyclohexylformamide, N-formylpiperidine, N-formylpyrrolidine, N-acetylmorpholine, N-methylpyrrolidone, N-ethylpyrrolidone, N-methylpiperidone and N-methylcaprolactam. N,N-dimethylformamide, N,N-diethylformamide, N,N-dimethylacetamide or N-methylpyrrolidone is preferably used as the solvent. N,N-dimethylformamide and N-methylpyrrolidone are particularly preferred.

It is also possible to employ mixtures of these compounds with other solvents.

The catalysts are in general used in an amount from 0.001 to 5 mol%, relative to the compound (III).

The reaction temperatures are in general between 50° and 200° C., preferably 90° to 160° C.

Suitable bases for the reaction of (II) with (III) are alkali metal and alkaline earth metal salts of aliphatic and aromatic carboxylic acids (for example acetates and benzoates).

Suitable cations $M^\oplus$ in the abovementioned formulae are protons and alkali metal and alkaline earth metal ions. $Na^\oplus$ and $K^\oplus$ are preferred.

"Alkyl" or "alkoxy" are preferably understood in the context of this invention as meaning radicals having 1 to 4 C atoms.

Suitable "halogen" Z and X is Cl, Br and I, particularly Br for Z and Cl for X.

Suitable aryl radicals are above all phenyl radicals which, for example, can be substituted by Cl or $CH_3$.

The compounds of the general formula (I) according to the invention have a high fluorescent power in solution and cause an excellent brightening effect when they are applied to natural and regenerated cellulose fibres, polyvinyl alcohol fibres and nitrogen-containing fibres, such as polyamide fibres, protein fibres and polyurethane fibres. They can also be used with paper, pulps, real and synthetic leather, casein polymers and resins, such as polyamide, polyurethane and melamine resins, and also with coatings, paints, soaps, synthetic detergents and sun lotions.

Treatment with the brighteners according to the invention can be effected in the following manner:

a) in a conventional manner by treatment in an aqueous solution, b) by fixing in the presence of heat, by steam treatment or acid shock, c) in the case of cellulose and polyamide fibres in a washing liquid which contains both a detergent or a soap and a compound of the general formula (I), d) together with a chemical bleaching agent or by addition of the compound (I) to a bleaching bath, e) if fibres or resins are treated in a bath, by dissolving the compound (I) in an organic solvent and, if necessary, water (use of the dyeing process in a solvent), f) in the case of paper, for example, by addition of a compound (I) to the paper pulp, by coating the surface or by sizing, g) in combination with other fluorescent brighteners for correcting the colour and/or for achieving various synergistic effects.

A feature of the compounds according to the invention is that they not only have a very good washing- and lightfastness, but also have an excellent resistance to chlorine and chlorites and a strong brightening power for cellulose and polyamide fibres. The brightening effect achieved is substantially better than that achieved with the brighteners known hitherto, in particular if a polyamide fibre in a washing liquid, which contains both a detergent (for example a synthetic and liquid detergent) or soap and the compound according to the invention, is simultaneously washed and brightened. Another feature of the compounds according to the invention is their strong affinity for both cellulose and also polyamide fibres at low and higher washing temperatures.

Even in amounts of only 0.001% of the material to be treated, these compounds sometimes cause a good brightening effect. In general, however, these compounds are used in an amount of 0.5% or more and in particular of 0.005 to 0.2%.

EXAMPLES

Example 1

5.16 g (10 mmol) of disodium 4,4'-dibromobiphenyl3,3'-disulphonate, 5.15 g( 25 mmol) of sodium styrene4-sulphonate, 3,3 g(40 mmol) of sodium acetate, 0.045 g (0.2 mmol) of palladium(II) acetate, 122 mg (0.4 mmol) of tri-o-tolylphosphine and 0.035 g of hydroquinone are heated under $N_2$ in 100 ml of DMF at 120° C. for 6 h. The mixture is evaporated to dryness, the residue is taken up in a little water and filtered, the filtrate is acidified and concentrated, and the solids is filtered off with suction and dried. 5.63 g (83%) of the compound of the formula

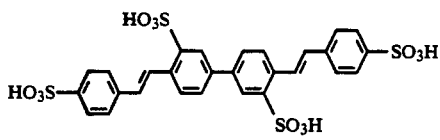

are obtained.

$^1$H-NMR (DMSO-d$_6$), $\delta$=7.25 (d, 2H), 7.5–7.8 (m, 10H), 7.96 (d, 2H), 8.2 (d, 2H), 8.34 (d, 2H)

UV (DMF) $\epsilon_{357nm}$=62,200

Example 2

The procedure is as in Example 1, but N-methylpyrrolidone is used instead of DMF and the reaction mixture is heated at 150° C. for 3 h. Yield: 5.4 g (80%).

Example 3

The procedure is as in Example 1, but sodium styrene-2-sulphonate is used instead of sodium styrene-4-sulphonate. The compound of the formula

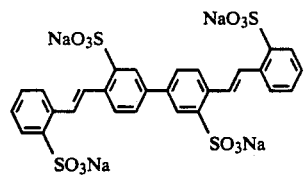

is obtained in a yield of 5.67 g (74%) as the product if the residue which remains after stripping off the DMF is stirred in a little NaCl solution, and the product is filtered off with suction and dried.

UV (DMF) $\epsilon_{345nm}$=56,300.

Example 4

The procedure is as in Example 3, but a 1:1 mixture of sodium styrene-4-sulphonate and sodium styrene-2-sulphonate is employed instead of sodium styrene-2-sulphonate. A product mixture of the formula

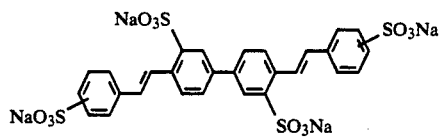

is obtained in which the sulpho groups in the styrene radicals are in each case either in the o- or p-position.

UV (DMF) $\epsilon_{346nm}$=58,000

Example 5

The procedure is as in Example 3, but a 1:1 mixture of sodium styrene-4-sulphonate and styrene is employed instead of sodium styrene-2-sulphonate. A mixture whose principal component is the compound of the formula

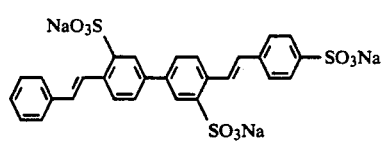

is obtained as the product.

Yield: 5.37 g

UV (DMF) $\epsilon_{354nm}$32 58,000

What is claimed is:

1. Bis-stilbene compounds of the formula (I)

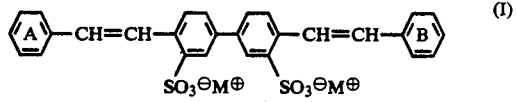

in which

M$\oplus$denotes a cation and at least one of the rings A or B contains a sulpho group.

2. Bis-stilbene compounds according to claim 1, characterized in that the rings A and B each contain a sulpho group.

3. Bis-stilbene compounds according to claim 1, characterized in that the sulpho groups are in the ortho- or para-position.

* * * * *